United States Patent [19]

McAlpine et al.

[11] Patent Number: 5,583,115
[45] Date of Patent: Dec. 10, 1996

[54] DIALKYLTIACUMICIN COMPOUNDS

[75] Inventors: James B. McAlpine, Libertyville; Jill E. Hochlowski, Green Oaks, both of Ill.

[73] Assignee: Abbott Laboratories, Abbott Park, Ill.

[21] Appl. No.: 437,761

[22] Filed: May 9, 1995

[51] Int. Cl.$^6$ .............................. A61K 31/70; C07H 17/08
[52] U.S. Cl. ................... 514/32; 514/23; 514/25; 536/7.1; 536/16.8
[58] Field of Search ............................ 536/7.1, 16.8; 514/23, 25, 32; 524/25

[56] References Cited

U.S. PATENT DOCUMENTS 4,918,174  4/1990  McAlpine et al. ................ 536/7.1

*Primary Examiner*—Elli Peselev
*Attorney, Agent, or Firm*—Mona Anand; Thomas D. Brainard

[57] ABSTRACT

Antimicrobial compounds having the formula

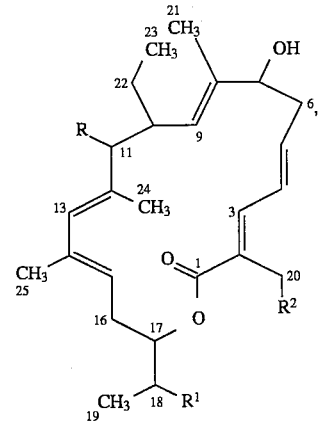

as well as pharmaceutical compositions comprising such compounds and methods of treating bacterial infection and colitis by the administration thereof.

17 Claims, 3 Drawing Sheets

DIALKYLTIACUMICIN COMPOUNDS

TECHNICAL FIELD

The present invention relates to alkylated antibiotic compounds derived from tiacumicin antibiotics and to methods useful for the preparation of such compounds, as web as to pharmaceutical compositions containing such compounds and the use thereof in treating bacterial infections.

BACKGROUND OF THE INVENTION

Certain antibiotics which are active against a broad range of Gram-positive and other bacteria are known to be produced by species of microorganisms isolated from soil samples throughout the world. There is an ongoing need, however, for new antimicrobial agents which show improved activity, have an improved or specific spectrum of efficacy, and/or exhibit more desirable pharmacokinetic properties when administered to a patient. One avenue of research has involved the derivatization of antibiotics in an effort to improve their antimicrobial properties.

In the case of antibacterial-associated or other nosocomial colitis, there is a particular need for antimicrobial agents which offer an improvement in long-term cure rate, i.e., which reduce the incidence of relapse often seen with commonly-used drugs such as vancomycin or metronidazole. Antibiotic-associated colitis, which can arise when normal gastrointestinal flora have been suppressed by antibiotic therapy, is often caused by the organism *Clostridium difficile*. It is therefore an aim of the present invention to provide antimicrobial agents which are particularly active against Clostridium while still permitting the re-establishment of some or all of the normal flora.

SUMMARY OF THE INVENTION

It has now been established that novel antimicrobial agents may be obtained by chemical modification of tiacumicins, which are antibiotics isolated from the fermentation broth and mycelium of *Dactylosporangium aurantiacum* subsp. *hamdenensis* subsp. nov. Tiacumicin antibiotics are described in U.S. Pat. No. 4,918,174 (issued Apr. 17, 1990 and incorporated herein by reference), and comprise the compounds tiacumicin A, tiacumicin B, tiacumicin C, tiacumicin D, tiacumicin E and tiacumicin F. The compounds of the present invention, which are derivatives of the above tiacumicins, are found to have in vitro activity against a variety of bacterial pathogens and in particular against Clostridium when evaluated in an assay utilizing Wilkins-Chalgren agar in anaerobic conditions. It is therefore expected that these compounds will be useful in the treatment of bacterial infections in mammals, and in particular in the treatment of certain instances of colitis.

Accordingly, in one aspect of the present invention, compounds are disclosed which have the formula:

(I)

as well as the pharmaceutically acceptable prodrugs thereof, wherein R is a substituent of the formula:

(Ia)

where
$R^{31}$, $R^{32}$ and $R^{33}$ are independently selected from hydrogen and $C_1$-to-$C_4$ alkanoyl;
$R^1$ is hydrogen or hydroxy; and
$R^2$ is hydrogen or a substituent of the formula:

where one of $R^{41}$ and $R^{42}$ is hydrogen and the other is a radical of the formula:

(Ic)

where $R^5$ is lower alkyl at each occurrence.

In a further aspect of the present invention, pharmaceutical compositions are disclosed which comprise a therapeutically effective amount of a compound of the invention in combination with a pharmaceutically acceptable carder.

In another aspect of the invention is disclosed a method of treating a Gram-positive bacterial infection, and particularly one caused by the pathogen *Clostridium difficile*, in a patient in need of such treatment, comprising administering to the patient a therapeutically effective amount of a compound of the invention.

In yet another aspect of the invention is disclosed a method of treating colitis in a patient in need of such treatment, comprising administering to the patient a therapeutically effective amount of a compound of the invention.

In still another aspect of the invention is disclosed a process for preparing the compounds of the invention which comprises the steps of (a) isolating tiacumicin from a fermentation medium; (b) purification of tiacumicin by precipitation or other methods; and (c) alkylating the 3'''- and 5'''- positions of tiacumicin.

BRIEF DESCRIPTION OF THE DRAWINGS

The following description of the present invention will be more readily appreciated in connection with the appended drawings, in which.

DETAILED DESCRIPTION OF THE INVENTION

Among the compounds of the present invention, preferred examples include those having the formulae:

and and any pharmaceutically acceptable prodrugs thereof. Particularly preferred among the compounds of the present invention are those in which $R^5$ is methyl or ethyl, and most particularly those in which $R^5$ is methyl.

Representative examples of the compounds of the present invention are the following tiacumicin derivatives:

3′″, 5′″-di-O-methyltiacumicin B;

3''', 5'''-di-O-methyltiacumicin C;
3''', 5'''-di-O-methyltiacumicin D;
3''', 5'''-di-O-methyltiacumicin E;
3''', 5'''-di-O-methyltiacumicin F;
3''', 5'''-di-O-ethyltiacumicin B;
3''', 5'''-di-O-ethyltiacumictn C;
3''', 5'''-di-O-ethyltiacumicin D;
3''', 5'''-di-O-ethyltiacumicin E; and
3''', 5'''-di-O-ethyltiacumicin F, and the pharmaceutically acceptable prodrugs thereof. Of these, and most preferred among the compounds of the present invention, is the compound 3''', 5'''-di-O-methyltiacumicin B, which has the structural formula:

and is regarded as the best mode of carrying out the present invention.

As used throughout this specification and in the appended claims, the following terms have the meanings specified:

The term "alkyl" as used herein refers to a monovalent straight-chain or branched-chain hydrocarbon radical of 1 to 12 carbon atoms including, but not limited to, methyl, ethyl, n-propyl, isopropyl, n-butyl, sec-butyl, isobutyl, tert-butyl, pentyl, hexyl, heptyl and the like.

The term "alkanoyl" as used herein refers to a monovalent radical of the formula —C(O)R", where R" is hydrogen or an alkyl group as defined above, including but not limited to acetyl, propionyl, isobutyryl and the like.

The term "$C_1$-to-$C_4$ alkanoyl" as used herein refers to an alkanoyl radical as defined above where R" is hydrogen or an alkyl group of 1 to 3 carbon atoms.

The term "lower alkyl" as used herein refers to an alkyl radical as defined above having to 6 carbon atoms.

The term "pharmaceutically acceptable prodrugs" as used herein refers to those prodrugs of the compounds of the present invention which are, within the scope of sound medical judgement, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in T. Higuchi and V. Stella, *Pro-drugs as Novel Delivery Systems*, Vol. 14 of the A.C.S. Symposium Series, and in Edward B. Roche, ed., *Bioreversible Carriers in Drug Design*, American Pharmaceutical Association and Pergamon Press, 1987, both of which are incorporated herein by reference.

Where appropriate, prodrugs of derivatives of compounds of the present invention may be prepared by any suitable method. For those compounds in which the prodrug moiety is an amino acid or peptide functionality, the condensation of the amino group with amino acids and peptides may be effected in accordance with conventional condensation methods such as the azide method, the mixed acid anhydride method, the DCC (dicyclohexyl-carbodiimide) method, the active ester method (p-nitrophenyl ester method, N-hydroxy-succinic acid imide ester method, cyanomethyl ester method and the like), the Woodward reagent K method, the DCC-HOBT (1-hydroxy-benzotriazole) method and the like. Classical methods for amino acid condensation reactions are described in M. Bodansky, Y. S. Klausner and M. A. Ondetti, *Peptide Synthesis*, Second Edition, NY, 1976.

Asymmetric centers may exist in the compounds of the present invention. Except where otherwise noted, the present invention contemplates the various stereoisomers and mixtures thereof. Accordingly, whenever a bond is represented nonstereospecifically, it is intended to encompass both orientations.

When used in the above or other treatments, a therapeutically effective amount of one of the compounds of the present invention may be employed in pure form or, where such forms exist, in pharmaceutically acceptable salt, ester or prodrug form. Alternatively, the compound may be administered as pharmaceutical compositions containing the compound of interest in combination with one or more pharmaceutically acceptable excipients. By a "therapeutically effective amount" of the compound of the invention is meant a sufficient amount of the compound to treat the targeted disorder, at a reasonable benefit/risk ratio applicable to any medical treatment. It will be understood, however, that the total daily usage of the compounds and compositions of the present invention will be decided by the attending physician within the scope of sound medical judgement. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a human or lower animal by oral administration may range from about 0.01 to about 100 mg/kg/day. More preferable doses may be in the range of from about 0.1 to about 10 mg/kg/day. If desired, the effective daily dose may be divided into multiple doses for purposes of administration; consequently, single dose compositions may contain such amounts or submultiples thereof as make up the daily dose.

The pharmaceutical compositions of the present invention comprise a compound of the invention and a pharmaceutically acceptable carrier or excipient, which may be administered orally, rectally, parenterally, intracistemally, intravaginally, intraperitoneally, topically (as by powders, ointments, or drops), bucally, or as an oral or nasal spray. By "pharmaceutically acceptable carrier" is meant a non-toxic solid, semi-solid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

Pharmaceutical compositions of this invention for parenteral injection include pharmaceutically acceptable sterile nonaqueous solutions or aqueous dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption such as aluminum monostearate and gelatin.

In some cases, in order to prolong the effect of the drug, it is deskable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides) Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carder such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose and acacia, c) humectants such as glycerol, d) disintegrating agents such as agar-agar, calcium carbonate, potato or tapioca starch, alginic acid, certain silicates and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols and sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, and sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Topical administration includes administration to the skin or mucosa, including surfaces of the lung and eye. Compositions for topical administration, including those for inhalation, may be prepared as a dry powder which may be pressurized or non-pressurized. In non-pressurized powder compositions, the active ingredient in finely divided form may be used in admixture with a larger-sized pharmaceutically acceptable inert carrier comprising particles having a size, for example, of up to 100 micrometers in diameter. Suitable inert carriers include sugars such as lactose. Desirably, at least 95% by weight of the particles of the active ingredient have an effective particle size in the range of 0.0 1 to 10 micrometers.

Alternatively, the composition may be pressurized and contain a compressed gas, such as nitrogen or a liquified gas propellant. The liquified propellant medium and indeed the total composition is preferably such that the active ingredient does not dissolve therein to any substantial extent. The pressurized composition may also contain a surface active agent. The surface active agent may be a liquid or solid non-ionic surface active agent or may be a solid anionic surface active agent. It is preferred to use the solid anionic surface active agent in the form of a sodium salt.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic. Methods to form liposomes are known in the art. See, for example, Prescott, Ed., *Methods in Cell Biology*, Volume XIV, Academic Press, New York, N.Y., 1976, p. 33 et seq.

The compounds of the invention may be prepared using one or more of the processes which follow. The tiacumicin s used as starting materials are available via fermentation as described in the above-referenced United States Patent No. 4,918,174. Tiacumicins can by alkylated by a variety of methods known to those well-versed in the art, provided, however, that the alkylation may require a starting material of high purity and a methodology suitable for selective alkylation.

Purification of the tiacumicins may be accomplished by precipitation from solution. The unpurified material is first dissolved in an appropriate organic solvent and then precipitated out in purified form by the addition of an appropriate organic co-solvent. Suitable organic solvents include alkyl halides such as dichoromethane, dichloroethane and the like and polar alkyl solvents such as methanol, ethyl acetate, acetone and the like. Suitable co-solvents include ethers and non-polar alkanes. The purified tiacumicin can readily be alkylated with diazomethane, dimethylsulfate, ethyl bromide, diethylsulfate, methyl iodide and the like. Diazomethane, for example, can be generated by a variety of commonly-known methods, and is a preferred alkylating agent.

The preparation of the compounds of the present invention is shown in Schemes I and II below. According to Scheme I, a compound of formula 1 (such as tiacumicin B, tiacumicin C, tiacumicin E or tiacumicin F) may be selectively alkylated on the aromatic phenol ring to give a compound of formula 2. (Tiacumcin D may be alkylated in an analogous manner.) According to Scheme II, tiacumicin B (3) may be treated with diazomethane in ether to give 3''', 5'''-di-O-methyltiacumicin B (4).

Scheme I

Scheme II

The compounds, processes and uses of the present invention will be better understood in connection with the following examples, which are intended as an illustration of and not a limitation upon the scope of the invention. Both below and throughout the specification, it is intended that citations to the literature are expressly incorporated by reference.

EXAMPLE 1

Purification of Tiacumicin B 0.61 g (0.578 mmol) of tiacumicin B (obtained by fermentation) where dissolved in 2 mL of methylene chloride. The resulting dark amber solution was added dropwise to a stirred solution of 15 mL of hexane at room temperature. After the addition was complete, the mixture was warmed to just below boiling and then allowed to cool to room temperature resulting in the precipitation of tiacumicin B. The purified material was collected by filtration and washed with hexane to give 158 mg of a pale tan solid. m.p. 106°–110° C. (decomposition). The proton NMR was consistent with the assigned structure.

EXAMPLE 2

3''', 5'''-Di-O-methyltiacumicin B

Figure 1:
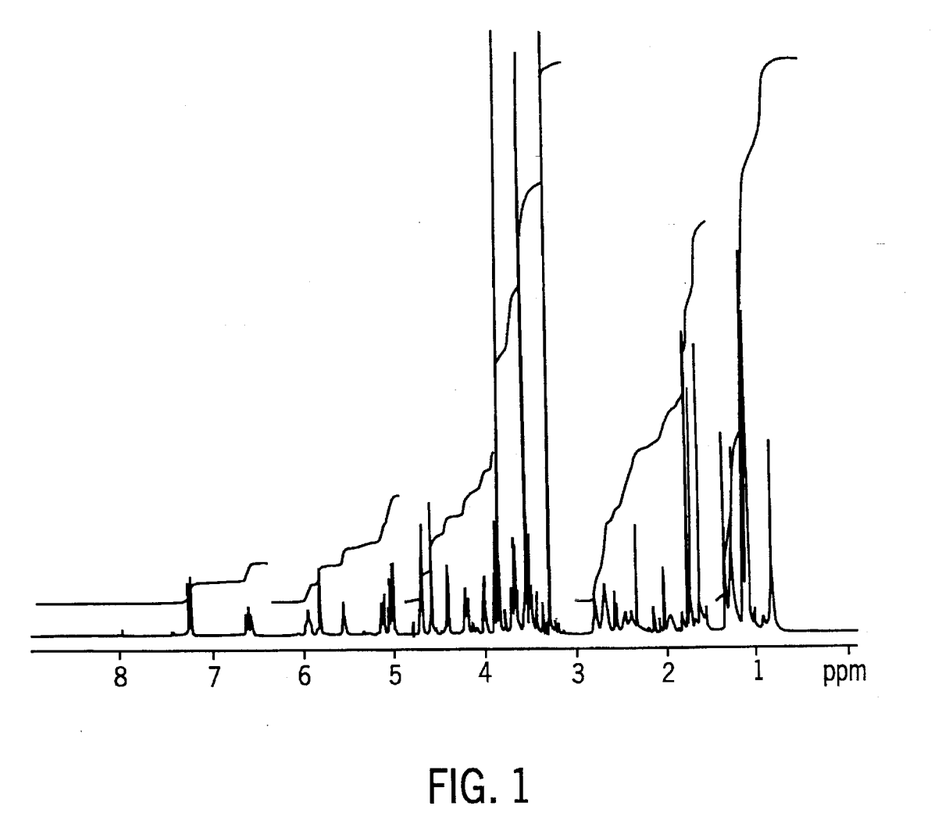
FIG. 1 is the hydrogen nuclear magnetic resonance spectrum of 3''', 5'''-di-O-methyltiacumicin B in methanol $d_4$.
Figure 2:
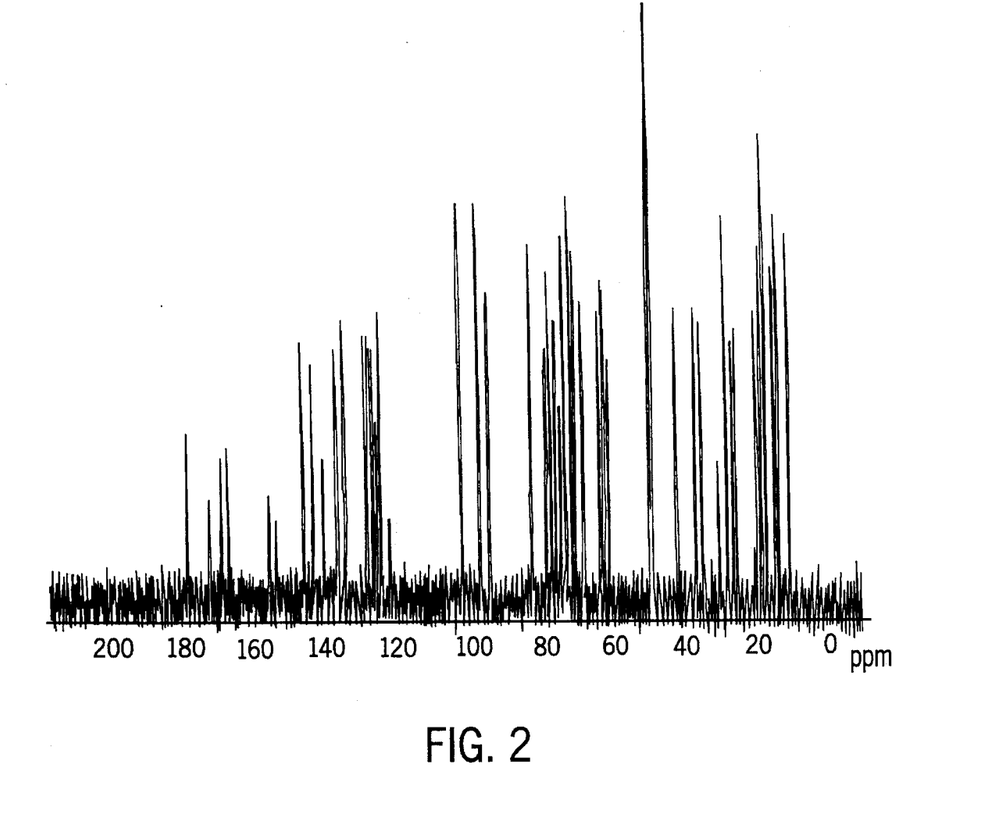
FIG. 2 is the carbon nuclear magnetic resonance spectrum of 3''', 5'''-di-O-methyltiacumicin B in methanol $d_4$.
Figure 3:
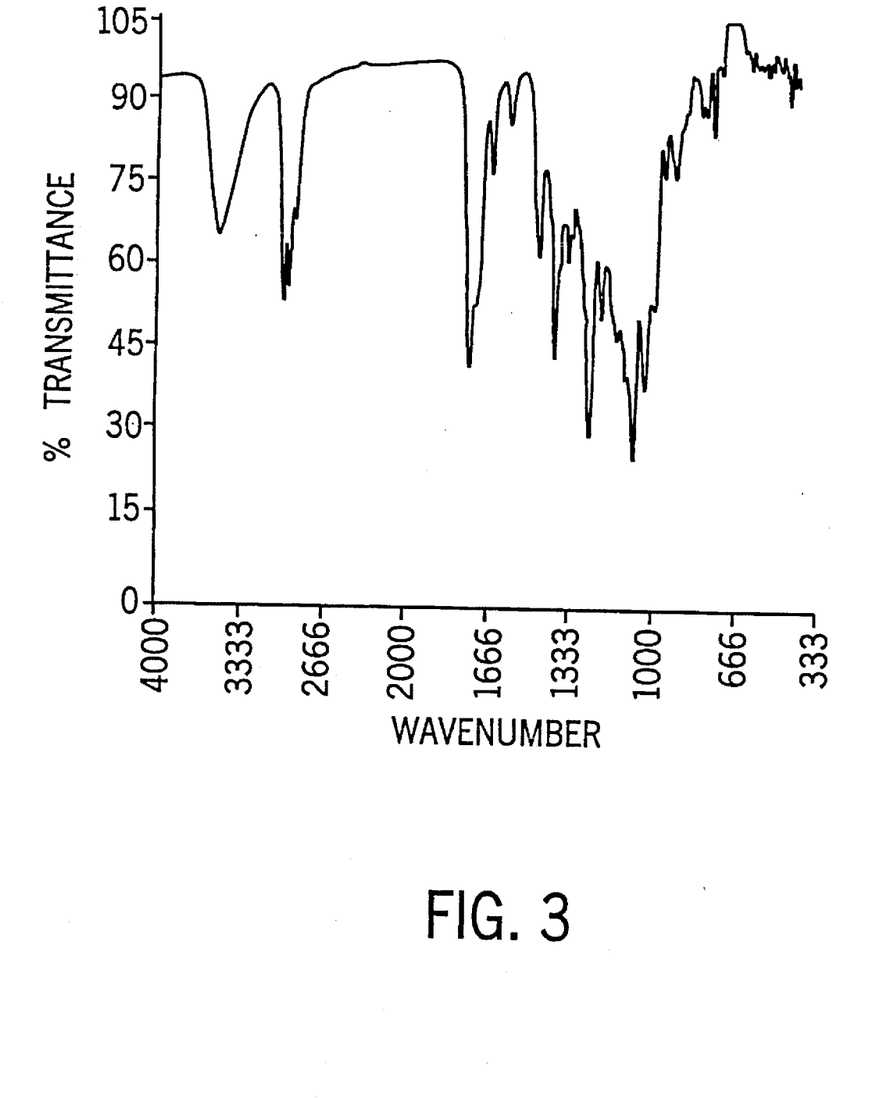
FIG. 3 is the infrared spectrum of 3''', 5'''-di-O-methyltiacumicin B neat (microscope acquisition).

A diazomethane solution was prepared by (a) adding 2.5 g of Diazald® (N-methyl-N-nitroso-p-toluenesulfonamide) in 25 mL of diethyl ether to a solution, warmed to 60°–65° C., of 2.5 g of potassium hydroxide dissolved in 4 mL of water and 5 mL of ethanol, and (b) collecting the distillate. 4.5 mL of the diazomethane distillate were then added to a solution of 158 mg of the compound resulting from Example 1 dissolved in 4.5 mL of methylene chloride at ambient temperature. After stirring for 15 minutes, the solution was aerated with nitrogen and concentrated under reduced pressure to give 410 mg of the title compound as a tan solid. m.p. 101°–107° C. (decomposition). The proton NMR, carbon NMR and infrared spectra, shown in FIGS. 1–3 hereof, were consistent with the assigned structural formula.

EXAMPLE 3

In Vitro Assay of Antibiotic Activity Against Aerobic and Facultative Bacteria For primary screening of compounds of the invention against aerobic and facultative bacteria, minimal inhibitory concentrations (MICs) were determined by the following agar dilution method: Series of two-fold dilutions of the test compounds were added to brain heart infusion agar. The agar plates were inoculated with approximately 10$^4$ organisms per spot of each of the organisms to be tested. These inoculated agar plates were then incubated at 37° C. for approximately 20 hours. The MICs were determined as the minimal concentration of test compound (in µg/mL) that inhhibited visible growth. The data, shown in Table 1, demonstrate that the compound of the present invention, di-O-methyltiacumicin B, is substantially less active than the starting material tiacumicin B against two bacteria commonly found in the normal gastrointestinal flora, *Enterococcus faecium* and *Streptococcus agalactiae*..

EXAMPLE 4

In Vitro Assay of Antibiotic Activity Against Anaerobic Bacteria

For primary screening of compounds of the invention against anaerobic bacteria such as Clostridium, minimal inhibitory concentrations (MICs) were determined by the following agar dilution method: Series of two-fold dilutions of the test compounds were added to WilkinsChalgren agar. The agar plates were inoculated with approximately 10$^5$ organisms per spot of each of the organisms to be tested. The inoculated agar plates were then incubated at 37° C. for approximately 48 hours. The MICs were determined as the minimal concentration of test compound (in µg/mL) that inhibited visible growth. The data, shown in Table 2, demonstrate that the compound of the present invention, di-O-methyltiacumicin B, has substantial activity against anaerobic pathogens and in particular against Clostridium species.

TABLE 1

MIC Data (µg/mL) for Aerobic and Facultative Bacteria

| Microorganism | Culture # | Tiacumicin B | Di-O-methyl-tiacumicin B | Vancomycin |
|---|---|---|---|---|
| *Staphylococcus aureus* | 1662 | 6.2 | 100 | 3.1 |
| *S. aureus* | 1664 | 6.2 | 50 | 1.56 |
| *S. aureus* | 1690 | 12.5 | 100 | 1.56 |
| *S. aureus* | 2130 | 12.5 | >100 | 3.1 |
| *S. aureus* | 2498 | 6.2 | >100 | 3.1 |
| *S. aureus* | 2124 | 6.2 | >100 | 3.1 |
| *S. aureus* (cipro res.) | 3384 | 12.5 | 100 | 1.56 |
| *S. epidermidis* | 1666 | 3.1 | 50 | 3.1 |
| *Enterococccus faecium* | 1668 | 6.2 | >100 | 3.1 |
| *Streptococcus bovis* | 1699 | 25 | >100 | 0.78 |
| *S agalactiae* | 1670 | 12.5 | >100 | 3.1 |
| *S. pyogenes* | 1671 | 25 | >100 | 3.1 |
| *S. pyogenes* (const.) | 1672 | 3.1 | 25 | 0.78 |
| *S. pyogenes* (inducible) | 2548 | 6.2 | 25 | 0.78 |
| *Micrococcus luteus* | 2517 | 0.2 | 0.1 | 3.1 |
| *M. luteus* | 2493 | 0.1 | 0.1 | 0.78 |
| *E. coli* Juhl | 1673 | >100 | >100 | >200 |
| *E. coli* SS | 2489 | >100 | >100 | 50 |
| *E.coli* DC-2 | 1674 | >100 | >100 | >200 |
| *E. coli* H560 | 1675 | >100 | >100 | >200 |
| *E. coli* KNK437 | 1676 | >100 | >100 | >200 |
| *Enterobacter aerogenes* | 1677 | >100 | >100 | >200 |
| *Klebsiella pneumoniae* | 2518 | >100 | >100 | >200 |
| *Providencia stuartii* | 1831 | >100 | >100 | >200 |
| *Pseudomonas aeruginosa* | 1679 | >100 | >100 | >200 |
| *P. aeruginosa* | 1680 | >100 | >100 | >200 |
| *P. aeruginosa* | 1681 | >100 | >100 | >200 |
| *P. aeruginosa* | 1682 | 12.5 | 100 | >200 |
| *P. cepacia* | 1684 | >100 | >100 | >200 |
| *Acinetobacter calcoaceticus* | 1845 | >100 | >100 | >200 |
| *P. aeruginosa* (cipro R) | 1919 | >100 | >100 | >200 |
| *P. aeruginosa* (cipro R) | 1920 | >100 | >100 | >200 |
| *Candida albicans* | 3622 | >100 | >100 | |
| *Mycobacterium smegmatis* | 5171 | 12.5 | 1.56 | |
| *Nocardia asteroides* | 5173 | 0.39 | 0.39 | |

TABLE 2

MIC Data (μg/mL) for Anaerobic Bacteria

| Microorganism | Culture # | Tiacumicin B | Di-O-methyl Tiacumicin B | Clindamycin | Vancomycin |
|---|---|---|---|---|---|
| Bacteriodes fragilis | 1756 | >128 | >2 | 1 | 32 |
| B. fragilis | 1757 | >128 | >2 | 1 | 32 |
| B. fragilis | 1758 | >128 | >2 | 0.5 | 16 |
| B. fragilis | 1999 | >128 | >2 | 1 | |
| B. vulgatus | 1762 | >128 | >2 | 0.03 | 32 |
| B. disiens | 1763 | 32 | >2 | 0.015 | 32 |
| B. thetaiotaomicron | 1764 | >128 | >2 | 4 | >64 |
| B. thetaiotamicron | 1765 | >128 | >2 | 4 | >64 |
| B. thetaiotaomicron | 1766 | >128 | >2 | 4 | >64 |
| B. loescheii | 1767 | 64 | >2 | 0.06 | 32 |
| B vulgatus | 2481 | >128 | >2 | 0.03 | 64 |
| B. bivius | 2483 | 128 | >2 | 0.015 | 32 |
| Fusobacterium nucleatum | 2478 | >128 | >2 | 0.12 | >64 |
| Fusobacterium species | 1770 | >128 | >2 | 0.12 | >64 |
| Veillonella parvula | 2479 | 64 | >2 | 0.06 | >64 |
| Propionibacterium acnes | 1775 | 4 | >2 | 0.06 | 0.5 |
| Peptostreptococcus asaccharolyticus | 1777 | 1 | >2 | 0.03 | 1 |
| P. magnus | 1778 | 0.5 | >2 | 1 | 0.5 |
| P. species | 1776 | 32 | >2 | 0.06 | 1 |
| P. anaerobius | 1780 | 0.008 | >2 | 0.06 | 0.5 |
| Clostridium perfringens | 1771 | 0.008 | 0.06 | 0.06 | >64 |
| C. perfringens | 1772 | 0.03 | 0.06 | 0.5 | 0.5 |
| C. perfringens | 1773 | 0.008 | 0.06 | 0.06 | 1 |
| C. ramosum | 2482 | >128 | >2 | 1 | 8 |
| C. difficile | 1496 | 0.06 | 0.25 | >32 | 0.5 |
| C. difficile | 1497 | 0.06 | 0.5 | >32 | 0.5 |
| C. difficile | 2025 | 0.06 | 0.5 | 4 | 0.5 |
| C. difficile | 2528 | 0.06 | 0.5 | 4 | 1 |
| C. difficile | 2529 | 0.06 | 0.5 | 4 | 1 |
| C. difficile | 1774 | 0.03 | 0.25 | 0.5 | 2 |
| C. difficile | 2480 | 0.06 | 0.25 | 4 | >64 |

EXAMPLE 5

In Vivo Activity Against Pseudomembranous Clostridium difficile—Induced Colitis One of the compounds of the present invention, di-O-methyltiacumicin B, was tested in an in vivo hamster model as follows: An infection of Clostridum difficile was induced in 32 hamsters by oral treatment with ciprofloxacin (200 mg/kg/day) for seven consecutive days (days 1–7). (Suppression of normal gastrointestinal bacteria by the ciprofloxacin permitted the drug-resistant C. difficile to predominate.) Five additional hamsters were segregated as a noninfected control group.

The infected animals were divided into three groups comprising (a) 10 untreated animals; (b) 15 vancomycin-treated animals (5 each at 20, 10 and 1 mg/kg/day orally on days 8–14); and (c) 10 animals treated with the compound of Example 2 (5 each at 10 and 1 mg/kg/day on days 8–14). The subject animals were monitored for (a) body weight (infected hamsters lose significant body mass), and (b) mortality (percent expiring by day 20).

TABLE 3

In vivo Hamster Model of Pseudomembranous Clostridium difficile Induced Colitis

| Treatment | Dose (mg/kg) | % Mortality | % Weight change, Day 22 |
|---|---|---|---|
| Cmpd of Example 2 | 10 | 60 | 140 |
| Cmpd of Example 2 | 1 | 20 | 154 |
| Vancomycin | 20 | 100 | ND |
| Vancomycin | 10 | 100 | ND |
| Vancomycin | 1 | 100 | ND |
| Infected Control | — | 90 | 139 |
| Non-infectedControl | — | 0 | 167 |

ND = no data; all animals had expired.

The results, shown above in Table 3, demonstrate the ability of the test compound di-O-methyltiacumicin B to effectively treat an antibiotic-associated colitis. Among untreated control animals, there was 90% mortality with infected animals, most of which rapidly developed a watery diarrhea and expired at approximately day 20. Hamsters treated with vancomycin at 1 mg/kg suffered more rapid mortality than hamsters treated at 10 or 20 mg/kg; overall, the majority of hamsters treated with vancomycin expired between days 17 and 22. Treatment with the compound of Example 2, on the other hand, was associated with a higher survival rate than either untreated infected controls or in hamsters treated with vancomycin.

Infected hamsters suffered significant decreases in body weight during acute illness. In general, surviving animals gained body mass at a normal rate following recovery, but still lagged behind the non-infected controls in weight. Hamsters treated with the compound of Example 2 at 1 mg/kg maintained body mass closest to that of non-infected controls.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art, and may be made without departing from the spirit and scope thereof.

What is claimed is:

1. A compound having the formula or a pharmaceutically acceptable prodrug thereof, wherein R is a substituent of the formula:

where

$R^{31}$, $R^{32}$ and $R^{33}$ are independently selected from the group consisting of hydrogen and $C_1$-to-$C_4$ alkanoyl;

$R^1$ is selected from the group consisting of hydrogen and hydroxy; and $R^2$ is selected from the group consisting of hydrogen and a substituent of the formula:

where one of $R^{41}$ and $R^{42}$ is hydrogen and the other is a radical of the formula:

where $R^5$ is lower alkyl at each occurrence.

2. A compound according to claim 1 wherein $R^5$ is selected from the group consisting of methyl and ethyl.

3. A compound according to claim 1 selected from the group consisting of:

and

-continued or a pharmaceutically acceptable prodrug thereof.

4. A compound according to claim 3 wherein $R^5$ is selected from the group consisting of methyl and ethyl.

5. The compound 3''',5'''-di-O-methyltiacumicin B or a pharmaceutically acceptable prodrug thereof.

6. A pharmaceutical composition comprising a therapeutically effective amount of a compound according to claim 1 in combination with a pharmaceutically acceptable carrier.

7. A pharmaceutical composition comprising a therapeutically effective amount of a compound according to claim 3 in combination with a pharmaceutically acceptable carder.

8. A pharmaceutical composition comprising a therapeutically effective amount of a compound according to claim 5 in combination with a pharmaceutically acceptable carder.

9. A method of treating a bacterial infection in a patient in need of such treatment, comprising administering to the patient a therapeutically effective amount of a compound according to claim 1.

10. A method of treating a bacterial infection in a patient in need of such treatment, comprising administering to the patient a therapeutically effective amount of a compound according to claim 3.

11. A method of treating a bacterial infection in a patient in need of such treatment, comprising administering to the patient a therapeutically effective amount of a compound according to claim 5.

12. A method of treating colitis in a patient in need of such treatment, comprising administering to the patient a therapeutically effective amount of a compound according to claim 1.

13. A method of treating colitis in a patient in need of such treatment, comprising administering to the patient a therapeutically effective amount of a compound according to claim 3.

14. A method of treating colitis in a patient in need of such treatment, comprising administering to the patient a therapeutically effective amount of a compound according to claim 5.

15. A method of treating an infection caused by *Clostridium difficile* in a patient in need of such treatment, comprising administering to the patient a therapeutically effective amount of a compound according to claim 1.

16. A method of treating an infection caused by *Clostridium difficile* in a patient in need of such treatment, comprising administering to the patient a therapeutically effective amount of a compound according to claim 3.

17. A method of treating an infection caused by *Clostridium difficile* in a patient in need of such treatment, comprising administering to the patient a therapeutically effective amount of a compound according to claim 5.

* * * * *

UNITED STATES PATENT AND TRADEMARK OFFICE
CERTIFICATE OF CORRECTION

PATENT NO. : 5,583,115
DATED : December 10, 1996
INVENTOR(S) : McAlpine, et. Al.

It is certified that error appears in the above-indentified patent and that said Letters Patent is hereby corrected as shown below:

Column 19, lines 31-40, change the structural formula therein to read:

Column 23, line 33, change "carder" to --carrier--.

Column 23, line 36, change "carder" to --carrier--.

Signed and Sealed this

Thirteenth Day of May, 1997

Attest:

BRUCE LEHMAN

Attesting Officer

Commissioner of Patents and Trademarks